(12) United States Patent
Cox et al.

(10) Patent No.: US 8,544,170 B2
(45) Date of Patent: Oct. 1, 2013

(54) METHOD OF FABRICATING A PERCUTANEOUS STIMULATION LEAD

(75) Inventors: Timothy J. Cox, Leonard, TX (US); John Erickson, Plano, TX (US); Enri Zhulati, Fort Worth, TX (US); Terry Daglow, Allen, TX (US); John Swanson, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 20 days.

(21) Appl. No.: 13/242,234

(22) Filed: Sep. 23, 2011

(65) Prior Publication Data
US 2012/0011711 A1  Jan. 19, 2012

Related U.S. Application Data

(63) Continuation of application No. 12/248,409, filed on Oct. 9, 2008, now Pat. No. 8,032,230.

(60) Provisional application No. 60/978,601, filed on Oct. 9, 2007.

(51) Int. Cl.
*H01R 43/00* (2006.01)
*H05K 13/00* (2006.01)

(52) U.S. Cl.
USPC ............ 29/854; 29/602.1; 29/831; 29/846; 600/372; 600/373; 607/63; 607/115; 607/156

(58) Field of Classification Search
USPC ........ 29/602.1, 831, 846, 854; 600/372–393; 607/63, 115–131
See application file for complete search history.

(56) References Cited

U.S. PATENT DOCUMENTS

| | | | |
|---|---|---|---|
| 5,217,010 A | 6/1993 | Tsitlik et al. | |
| 5,417,719 A * | 5/1995 | Hull et al. | 607/46 |
| 6,985,775 B2 | 1/2006 | Reinke et al. | |
| 7,174,219 B2 | 2/2007 | Wahlstrand et al. | |
| 7,363,090 B2 | 4/2008 | Halperin et al. | |
| 7,450,992 B1 * | 11/2008 | Cameron | 607/46 |
| 7,734,354 B1 * | 6/2010 | Cox | 607/116 |
| 7,962,224 B1 * | 6/2011 | Blischak | 607/116 |
| 8,200,343 B2 * | 6/2012 | Gerber et al. | 607/126 |
| 2003/0083726 A1 | 5/2003 | Zeijlemaker et al. | |

(Continued)

OTHER PUBLICATIONS

Bhachu, Dewinder S., et al., "Implantable Pulse Generators (Pacemakers) and Electrodes: Safety in the Magnetic Resonance Imaging Scanner Environment," Journal of Magnetic Resonance Imaging, 12:201-204 (2000).

(Continued)

*Primary Examiner* — Paul D Kim

(57) ABSTRACT

In one embodiment, a percutaneous stimulation lead for applying electrically stimulation pulses to tissue of the patient comprises: a plurality of electrode assemblies electrically coupled to a plurality of terminals through a plurality of conductors of the stimulation lead, wherein each electrode assembly is disposed in an annular manner around the lead body and each electrode assembly comprises (i) an electrode adapted to deliver electrical stimulation to tissue of a patient, (ii) an interior conductive layer, and (iii) a dielectric layer disposed between the electrode and the interior conductive layer; the electrode and interior conductive layer being capacitively coupled, the dielectric layer further comprising an inductor, the inductor being electrically connected to one of the plurality of conductors through the interior conductive layer, and the inductor being electrically coupled to the electrode.

8 Claims, 12 Drawing Sheets

(56) References Cited

U.S. PATENT DOCUMENTS

| | | |
|---|---|---|
| 2003/0144716 A1 | 7/2003 | Reinke et al. |
| 2003/0144720 A1 | 7/2003 | Villaseca et al. |
| 2005/0027340 A1 | 2/2005 | Schrom et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2007/0088416 A1 | 4/2007 | Atalar et al. |
| 2007/0112398 A1 | 5/2007 | Stevenson et al. |
| 2007/0185556 A1 | 8/2007 | Williams et al. |
| 2007/0208383 A1 | 9/2007 | Williams |
| 2007/0299490 A1 | 12/2007 | Yang et al. |
| 2008/0009905 A1 | 1/2008 | Zeijlemaker |
| 2008/0033497 A1 | 2/2008 | Bulkes et al. |
| 2008/0116997 A1 | 5/2008 | Dabney et al. |
| 2008/0119919 A1 | 5/2008 | Atalar et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |
| 2012/0110846 A1* | 5/2012 | Franz et al. .............. 29/876 |

OTHER PUBLICATIONS

Buchli R., et al., "Heating Effects of Metallic Implants by MRI Examinations," Magnetic Resonance in Medicine, 7, 255-261 (1988).

Finelli, Daniel, et al."MR Imaging-Related Heating of Deep Brain Stimulation Electrodes: In Vitro Study," Am. J. Neuroradiol, 23:1795-1802, Nov./Dec. 2002.

Ho, Henry S., "Safety of Metallic Implants in Magnetic Resonance Imaging," Journal of Magnetic Resonance Imaging, 14: 472-477 (2001).

\* cited by examiner

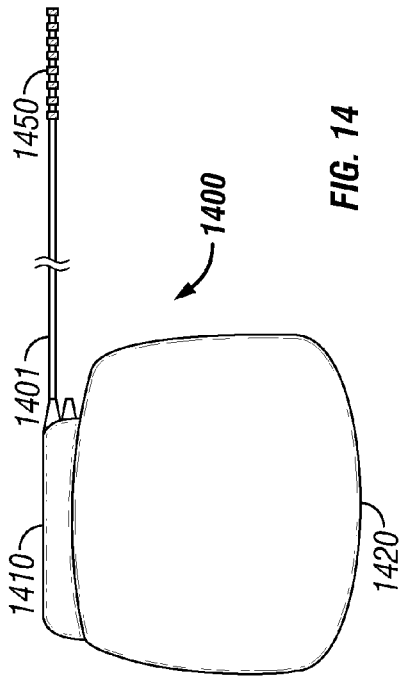
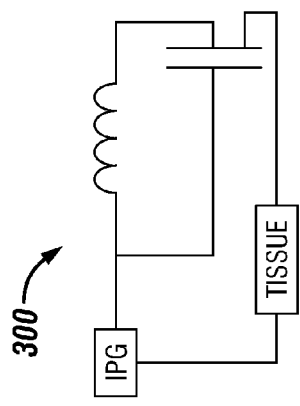

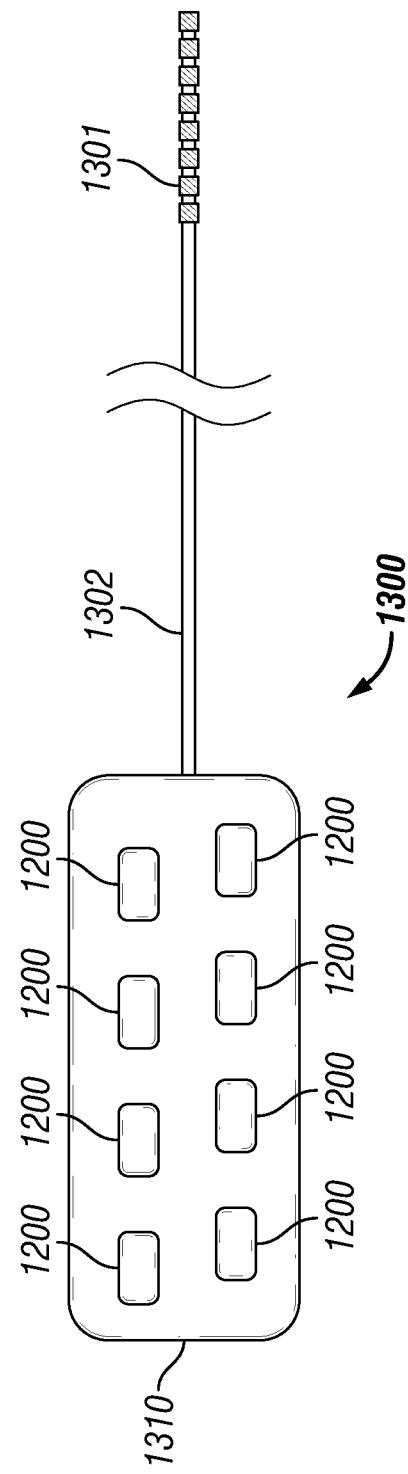

METHOD OF FABRICATING A PERCUTANEOUS STIMULATION LEAD

CROSS-REFERENCE TO RELATED APPLICATIONS

This application is a continuation of U.S. application Ser. No. 12/248,409, filed Oct. 9, 2008, now U.S. Pat. No. 8,032,230, which claims the benefit of U.S. Provisional Application No. 60/978,601, filed Oct. 9, 2007, the disclosure of which are incorporated herein by reference.

BACKGROUND

The present application is generally related to limiting MRI induced current in a stimulation lead such as a neurostimulation lead, a cardiac stimulation lead, and/or the like.

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or several leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

There are concerns related to the compatibility of neurostimulation systems with magnetic resonance imaging (MRI). MRI generates cross-sectional images of the human body by using nuclear magnetic resonance (NMR). The MRI process begins with positioning the patient in a strong, uniform magnetic field. The uniform magnetic field polarizes the nuclear magnetic moments of atomic nuclei by forcing their spins into one of two possible orientations. Then an appropriately polarized pulsed RF field, applied at a resonant frequency, forces spin transitions between the two orientations. Energy is imparted into the nuclei during the spin transitions. The imparted energy is radiated from the nuclei as the nuclei "relax" to their previous magnetic state. The radiated energy is received by a receiving coil and processed to determine the characteristics of the tissue from which the radiated energy originated to generate the intra-body images.

Currently, most neurostimulation systems are designated as being contraindicated for MRI, because the time-varying magnetic RF field causes the induction of current which, in turn, can cause significant heating of patient tissue due to the presence of metal in various system components. The induced current can be "eddy current" and/or current caused by the "antenna effect." As used herein, the phrase "MRI-induced current" refers to eddy current and/or current caused by the antenna effect.

"Eddy current" refers to current caused by the change in magnetic flux due to the time-varying RF magnetic field across an area bounding conductive material (i.e., patient tissue). The time-varying magnetic RF field induces current within the tissue of a patient that flows in closed-paths. When conventional pulse generator 103 (as shown in FIG. 1) and conventional implantable lead 104 are placed within tissue in which eddy currents are present, the implantable lead and the pulse generator provide a low impedance path for the flow of current. Electrodes 102 of the lead provide conductive surfaces that are adjacent to current paths 101 within the tissue of the patient. The electrodes 102 are coupled to the pulse generator 103 through a wire conductor within the implantable lead 104. The metallic housing (the "can") of the pulse generator 103 provides a conductive surface in the tissue in which eddy currents are present. Thus, current can flow from the tissue through the electrodes 102 and out the metallic housing of the pulse generator 103. Because of the low impedance path and the relatively small surface area of each electrode 102, the current density in the patient tissue adjacent to the electrodes 102 can be relatively high. Accordingly, resistive heating of the tissue adjacent to the electrodes 102 can be high and can cause significant, irreversible tissue damage.

Also, the "antenna effect" can cause current to be induced which can result in undesired heating of tissue. Specifically, depending upon the length of the stimulation lead and its orientation relative to the time-varying magnetic RF field, the wire conductors of the stimulation lead can each function as an antenna and a resonant standing wave can be developed in each wire. A relatively large potential difference can result from the standing wave thereby causing relatively high current density and, hence, heating of tissue adjacent to the electrodes of the stimulation lead.

SUMMARY

In one embodiment, a percutaneous stimulation lead for applying electrically stimulation pulses to tissue of the patient comprises: a plurality of electrode assemblies electrically coupled to a plurality of terminals through a plurality of conductors of the stimulation lead, wherein each electrode assembly is disposed in an annular manner around the lead body and each electrode assembly comprises (i) an electrode adapted to deliver electrical stimulation to tissue of a patient, (ii) an interior conductive layer, and (iii) a dielectric layer disposed between the electrode and the interior conductive layer; the electrode and interior conductive layer being capacitively coupled, the dielectric layer further comprising an inductor, the inductor being electrically connected to one of the plurality of conductors, and the inductor being electrically coupled to the electrode.

BRIEF DESCRIPTION OF THE DRAWING

FIG. 3 depicts a circuit diagram associated with the electrode of the lead shown in FIG. 2 according to one representative embodiment.

FIG. 4 depicts another circuit diagram for mitigating MRI induced current according to one representative embodiment.

FIG. 13 depicts a paddle-style stimulation lead according to one representative embodiment.

FIG. 14 depicts a stimulation system according to one representative embodiment.

DETAILED DESCRIPTION

Some representative embodiments are directed to a MRI compatible lead for stimulation of a patient. Specifically, some representative embodiments provide passive electrical components within the hollow volume defined by a "wrapped around" electrode of a percutaneous lead. Preferably, an inductor is provided within the space defined by the electrode. Additionally, a capacitive reactance also connects one end of the inductor to the electrode. The values of the inductance and capacitance of the passive electrical components are preferably selected based upon the expected operating frequency (f) of a particular class of MRI systems. By inserting a series tuned LC impedance between one electrode and the IPG, MRI induced current between the electrode and the IPG may be reduced. Although a tuned LC circuit is employed according to one representative embodiment, other embodiments may implement other MRI-induced current filtering circuits using passive electrical components within the confines of the volume defined by an electrode of the lead.

Figure 1:
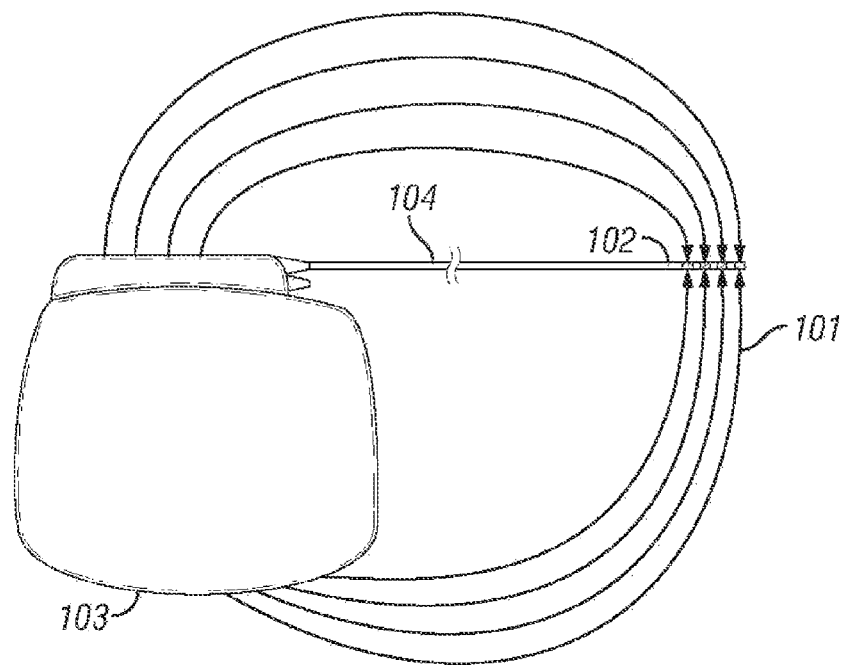
FIG. 1 depicts a pulse generator and implantable lead subjected to eddy current induced by the time-varying RF field of a MRI scan.
Figure 2:
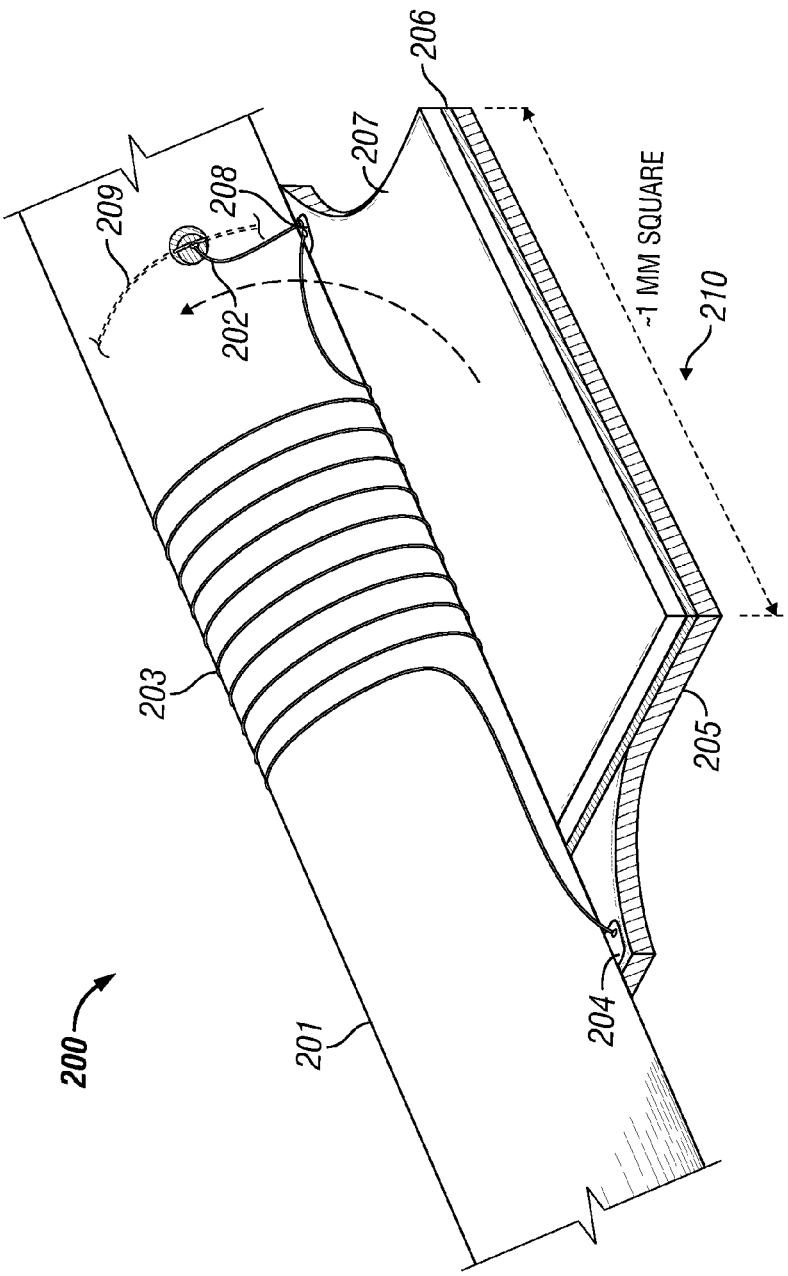
FIG. 2 depicts a portion of a stimulation lead adapted to mitigate MRI induced current according to one representative embodiment.

FIG. 2 depicts lead 200 that comprises passive electrical components within the confines of the space defined by a band or ring-like electrode for mitigating MRI induced current according to one representative embodiment. Lead 200 comprises lead body 201 of insulative material. The insulative material of lead body 201 encloses or encapsulates the wire conductors (including conductor 209) that conduct electrical pulses between the electrodes and terminals of the lead. Lead body 201 can be fabricated using any conventional or known fabrication technique or any later developed technique. An example of a suitable fabrication technique for forming a lead body 201 with embedded wire conductors can be found in U.S. Pat. No. 7,149,585 which is incorporated herein by reference.

Lead 200 comprises capacitive electrode assembly 210. Capacitive electrode assembly 210 comprises electrode 205, a layer of dielectric material 206, and interior metal component or layer 207. Electrode 205, dielectric material 206, and interior metal component 207 are shown in a flat configuration in FIG. 2 for the sake of clarity. After the completion of the fabrication of lead 201, electrode 205, dielectric material 206, and interior metal component 207 are preferably disposed in a band or ring-like manner around lead body 201.

Electrode 205 is disposed on the exterior of capacitive electrode assembly 210 to provide electrical stimulation from the IPG to tissue of the patient. Electrode 205 is preferably fabricated using platinum or a platinum-iridium alloy, although any suitably conductive and biostable, biocompatible material may be employed. Interior metal component 207 can be fabricated using a similar conductive material.

Dielectric material 206 electrically insulates electrode 205 from interior metal component 207. In one embodiment, the thickness of dielectric material is approximately 100 microns, although any suitable thickness may be employed. Suitable materials for dielectric material 206 include materials commonly utilized in lead fabrication technologies such as polyurethanes, silicone-based materials (e.g., PurSil™ and CarboSil™), polyethylene, polyimide, polyvinylchloride, PTFE, EFTE, etc.

In this embodiment, capacitive electrode assembly 210 provides the capacitive reactance for an LC circuit as discussed above. The capacitance of the electrode 205, dielectric material 206, and interior component 207 is approximately equal to: $C = \in A/d$, where $\in$ is the permittivity of the dielectric material, A is the surface area of interior metal component 207, and d is the thickness of the dielectric material.

Wire 203 is wrapped around a region of lead body 201 to form an inductor. Upon completion of the fabrication of lead 200, wire 203 is preferably enclosed by interior metal layer 207, dielectric material 206, and electrode 205. Wire 203 is preferably coated with an insulative polymer or other suitable insulator. The insulative material at one end of wire 203 is stripped and the end of wire 203 is preferably welded to electrode at location 204. The insulative material at the other end of wire is also stripped and the other end is preferably welded to interior metal component 207 at location 208. Wire 203 can alternatively be welded or otherwise electrically coupled to a conductor of lead body 201. Wire 203 comprises a number of turns about lead body 201 between location 204 and location 208. The inductance provided by the inductor is related to the square of the number of turns of wire and the outside diameter of lead body 201. The inductance can be obtained from tables or approximated by the following equation: $L = \mu_0 \mu_r N^2 A/l$, where $\mu_0$ is the permeability of free space, $\mu_r$ is the permeability of the lead body, N is the number of turns of the wire, A is the cross sectional area of the lead, and L is the length of the portion of wire that is wrapped about the lead body.

Additionally, jumper wire 202 is welded to interior metal component 207 at location 208. Jumper wire 202 is used as a convenient intermediate electrical connector to connect to wire conductor 209 that is embedded within the lead body 201. Preferably, a small aperture is formed in the insulative material of lead body 201 using a suitable laser to expose a small portion conductor 209. One end of jumper wire 202 is placed within the aperture and welded to conductor 209 at that location. The other end of jumper wire 202 is then welded to interior metal component 207 at location 208. Jumper wire 202 is also preferably maintained underneath electrode assembly 210 upon completion of the fabrication of lead 200.

FIG. 3 depicts equivalent circuit representation 300 for the lead shown in FIG. 2. Circuit 300 includes a series LC component as formed by capacitive electrode assembly 210 and wire wrapped inductor 203. As seen in FIG. 3, one plate of the capacitor is coupled to the IPG and the tissue of the patient while the other plate of the capacitor is coupled to one end of the inductor. Additionally, a return path is shown from a plate of the capacitor through tissue of the patient to the IPG. Preferably, the capacitance and inductance of circuit 300 are selected to resonate at a particular frequency that corresponds to an anticipated MRI operating frequency (e.g., 63.9 MHz). The appropriate values for resonance at the MRI operating frequency can be estimated using the following equation: $f=1/(2*\pi*sqrt(L\times C))$, where f is MRI operating frequency, L is the inductance provided by the wrapped wire, and C is the capacitance of electrode assembly 210.

Figure 8:
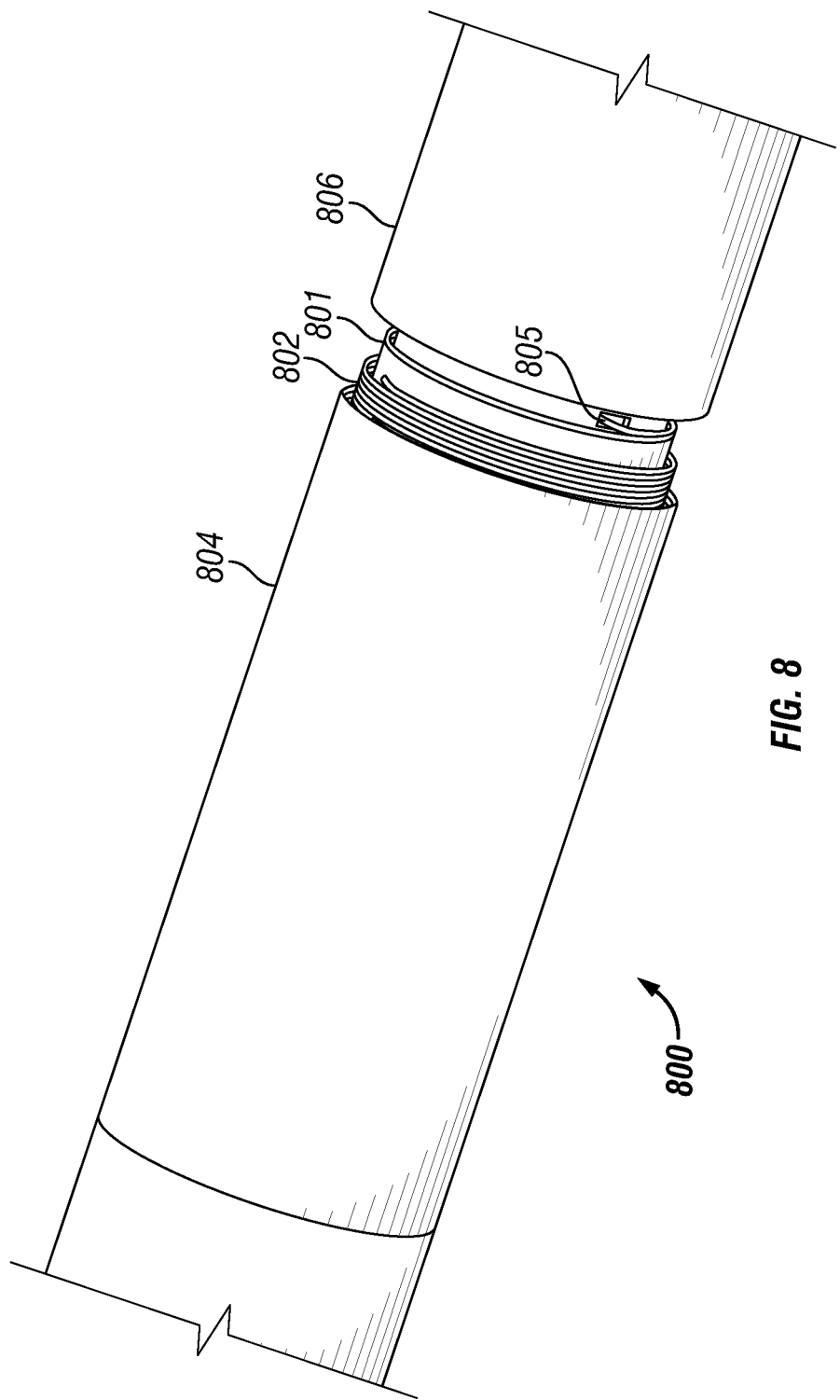
FIG. 8 depicts an electrode assembly according to one representative embodiment.
Figure 9:
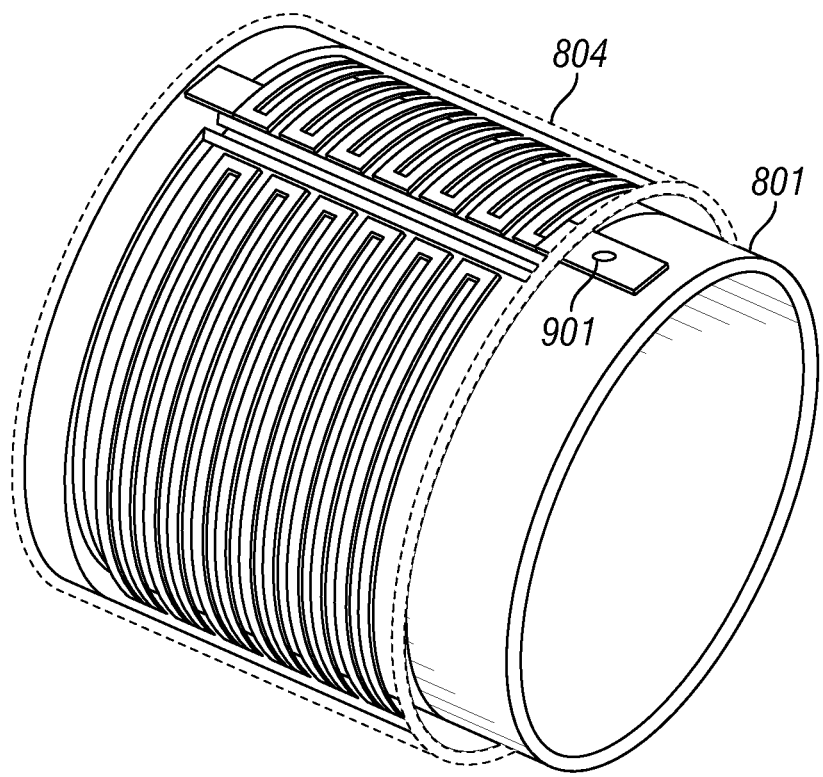
FIG. 9 depicts another electrode assembly according to one representative embodiment.

In some alternative embodiments, the wire-inductor is formed between the capacitive plates of the electrode assemblies (preferably within dielectric material). FIG. 8 depicts electrode assembly 800 according to one representative embodiment. Electrode assembly 800 comprises inner conductive layer 801 (e.g., a metal cylinder). During the lead fabrication process, inner conductive layer 801 is electrically coupled to a respective wire 805 of lead body 806. Intermediate layer 802 comprises a wire inductor. The wire inductor is preferably formed by multiple windings of insulated wire. One end of the wire inductor is stripped and electrically coupled to the outer surface of inner conductive layer 801. The other end of wire inductor is stripped and electrically coupled to the inner surface of electrode layer 804. In another embodiment, layer 802 can be implemented by employing one or more inductive winding or traces 901 disposed within flex film layers disposed between conductive and electrode layers 801 and 804 as shown in FIG. 9. Electrode layer 804 is preferably an annular metal component that is intended to contact tissue of the patient to deliver electrical stimulation, although a conductive polymer electrode surface could also be employed.

Current in a stimulation pulse flows through the wire conductor of the lead body, through the inner conductive layer 801, through the inductor of layer 802, and through electrode layer 804 to tissue of the patient. At stimulation frequencies, current flowing through layer 801, the inductor of layer 802, and layer 804 experience relatively little impedance. At MRI frequencies, current flowing through layer 801, the inductor, and layer 804 experiences significant impedance and, hence, is substantially attenuated. Preferably, the inductance and capacitance of electrode assembly 800 are selected such that electrode assembly 800 resonates at a frequency that corresponds to the operational frequency of a given class of MRI systems.

Figure 10:
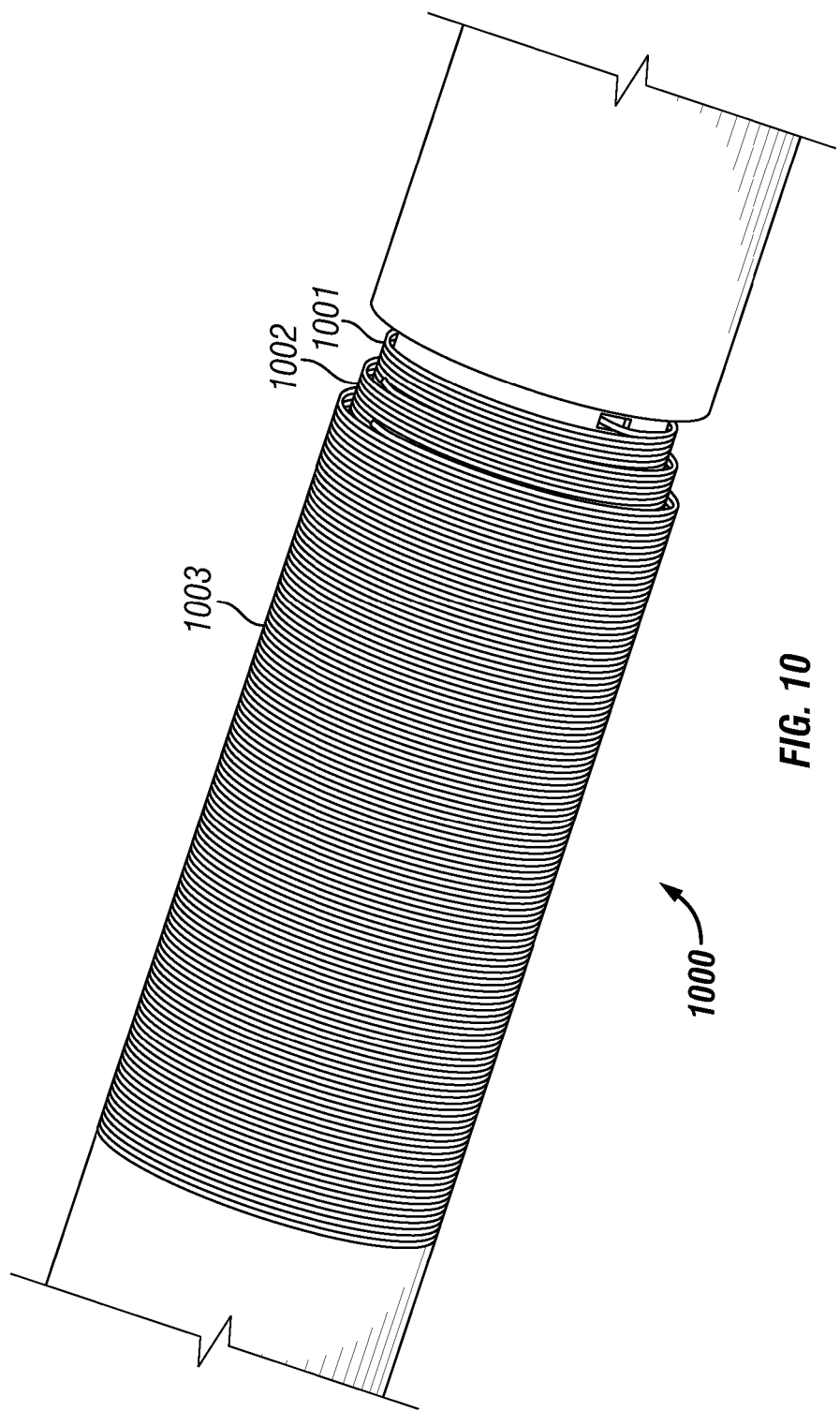
FIGS. 10 and 11 depict another electrode assembly using wire assemblies according to some representative embodiments.

FIG. 10 depicts electrode assembly 1000 according to another representative embodiment. Electrode assembly 1000 is conceptually similar to electrode assembly 800, although another fabrication technique is employed. Specifically, electrode assembly 1000 comprises inner conductive layer 1001, wire inductor layer 1002, and outer electrode layer 1003. The difference between electrode assembly 800 and electrode assembly 1000 is that all three layers 1001, 1002, and 1003 are preferably fabricated using a single wire.

In a preferred embodiment, an aperture is made to expose an interior wire of a stimulation lead. One end of insulated wire is electrically coupled to the exposed wire of the stimulation lead (e.g., using laser welding). Then, the insulation of the wire is preferably removed as the wire is wrapped about the stimulation lead to form layer 1001. The removal of the insulation may occur using mechanical means (e.g., grinding) or by applying heat or laser ablation, as examples, to remove the insulation as examples. The wire is preferably wrapped to produce a dense coil such that each discrete turn about the stimulation lead is in mechanical contact with a prior turn. After layer 1001 is formed, the winding continues without the removal of the insulation thereby forming layer 1002. The winding of the wire continues and the removal of the insulation is resumed thereby forming layer 1003. The wire may be severed and the terminal end of the wire can be welded to the surface of layer 1003 to complete electrode assembly 1000.

In one alternative embodiment, a non-insulated wire may be used in a reverse process where insulative material is applied to the wire when the winding of layer 1002 occurs. For example, a UV curing process may be employed to secure the insulative material to the wire as the wire is being applied to the stimulation lead. In another embodiment, a separate non-insulated wire, an insulated wire, and another non-insulated wire are successively wound about the stimulation lead and welded together to form the various layers 1001, 1002, and 1003. Also, in some embodiments, multiple windings of the wire(s) may occur on top of each other for any one or all of layers 1001, 1002, and 1003. For example, layer 1002 may comprise multiple concentric bands to increase the inductance of inductive layer 1002.

Figure 11:
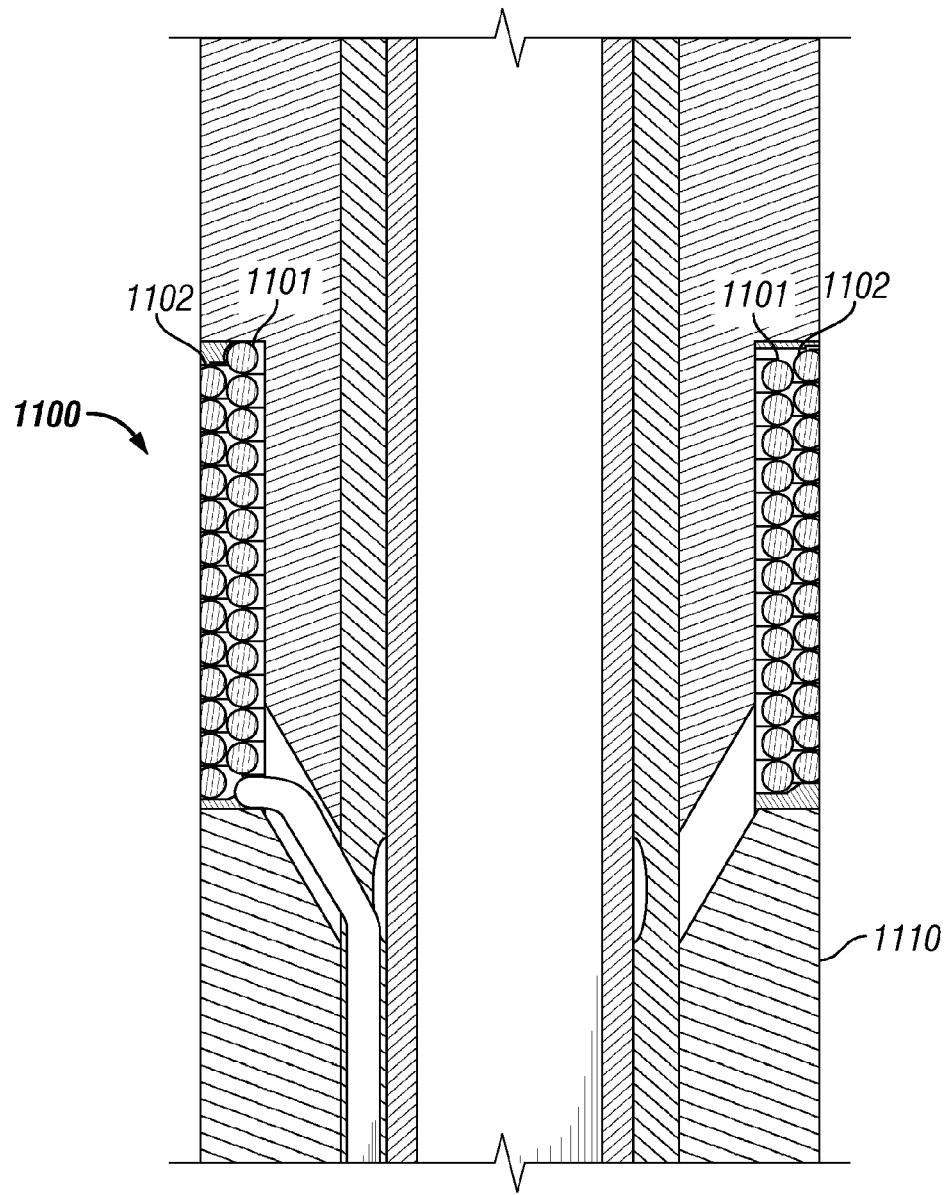

FIG. 11 depicts electrode assembly 1100 according to another representative embodiment. Electrode assembly 1100 depicts a capacitor formed between two wire layers 1101 and 1102. Specifically, a single wire is electrically coupled to an interior wire conductor of the lead and wrapped about lead body 1110 in two layers. In one preferred embodiment, an insulated Pl-Ir wire having an outside diameter (OD) of 0.003" is coiled twice about lead body 1110 with thirteen turns to create an electrode having a length of approximately 0.040". The capacitance of electrode assembly 1100 is defined by the capacitance between inner layer 1101 and outer layer 1102. The inductance is provided by the various convolutions or turns about lead body 1110. In one embodiment, the individual strands in each layer are glued together with adjacent strands. The insulative coating of the wire is removed on the exterior layer 1102 thereby exposing the metal wire. The exposed wire surface forms the electrode surface to conduct stimulation pulses to tissue of the patient. In a preferred embodiment, the OD profile of the electrode assembly 1100 is approximately 0.055" and is equal to the OD of the lead 1100.

Figure 12:
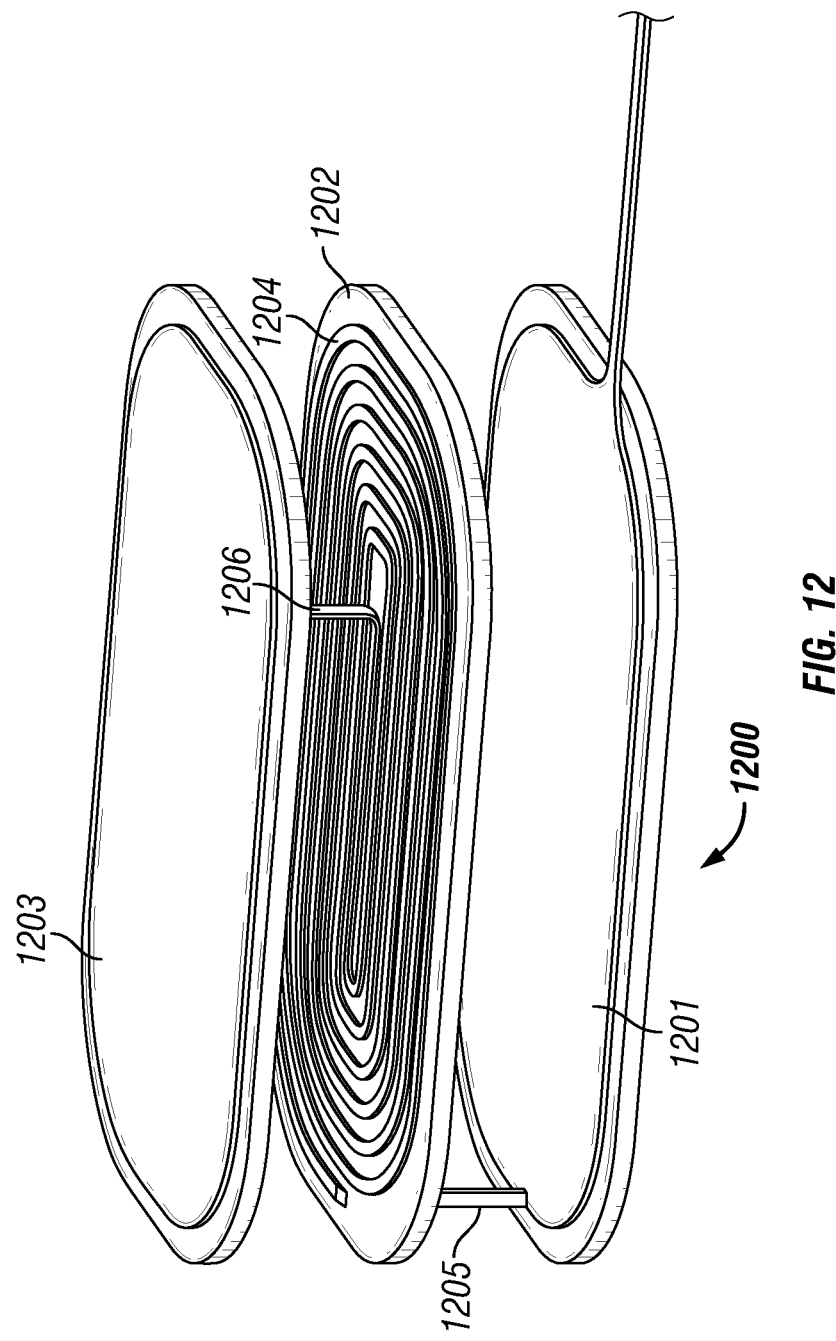
FIG. 12 depicts a planar electrode assembly suitable for a paddle-style lead according to one representative embodiment.

Although some embodiments have been discussed in terms of electrode assemblies adapted for percutaneous leads, other embodiments may provide electrode assemblies adapted for paddle-style leads. Electrode assembly 1200 (as shown in FIG. 12) comprises planar inner conductive layer 1201, inductive layer 1202, and electrode layer 1203. Inductive layer 1202 comprises inductive winding 1204, and layer connectors 1205 and 1206 for connecting to layers 1201 and 1203. In one embodiment, inductive layer 1202 is fabricated using photolithographic processes to deposit metallic material on a flexible, insulative substrate according to the desired pattern of the planar inductive winding 1204. After depositing the material on the insulative substrate, another insulative film is applied over the top and a laminate structure is formed. In some embodiments, multiple layers of insulative material and conductive windings (e.g., as deposited using a photolithographic process or an ink-jet deposition process) are provided to increase the inductance of layer 1202. In one embodiment, platinum iridium or other suitable metal material or alloy could be employed for the conductive windings. In other embodiments, a conductive composite plastic or an intrinsically conductive polymer could be employed for the conductive windings. Layer connections 1205 and 1206 are preferably left exposed and subsequently are preferably welded to layers 1201 and 1203.

FIG. 13 depicts paddle lead 1300 according to one representative embodiment. Paddle lead 1300 comprises paddle structure 1310 that holds electrode assemblies 1200 in a fixed arrangement. Any suitable number of electrode assemblies 1200 can be employed on the paddle structure of lead in any suitable pattern. Electrode assemblies 1200 are electrically coupled through the conductors of lead body 1302 to terminals 1301.

Other circuit designs may be employed to reduce MRI induced current according to other representative embodiments. FIG. 4 depicts circuit diagram 400 for mitigating MRI induced current according to one representative embodiment. Circuit diagram 400 depicts a plurality of terminals 401 ($T_1$-$T_N$) electrically coupled to a plurality of electrodes 402 ($E_1$-$E_N$) through lead wires 403. Each electrode 402 is electrically coupled through a respective capacitor 404 to the next electrode 402 (e.g., electrode $E_1$ is electrically coupled through a capacitor to electrode $E_2$). The capacitance of the capacitors 404 is selected such that capacitors exhibit a relatively high impedance at stimulation frequencies and a relatively low impendence at MRI frequencies. When electrodes 402 are electrically coupled in this manner, a reduction in MRI induced heating has been observed.

Figure 5:
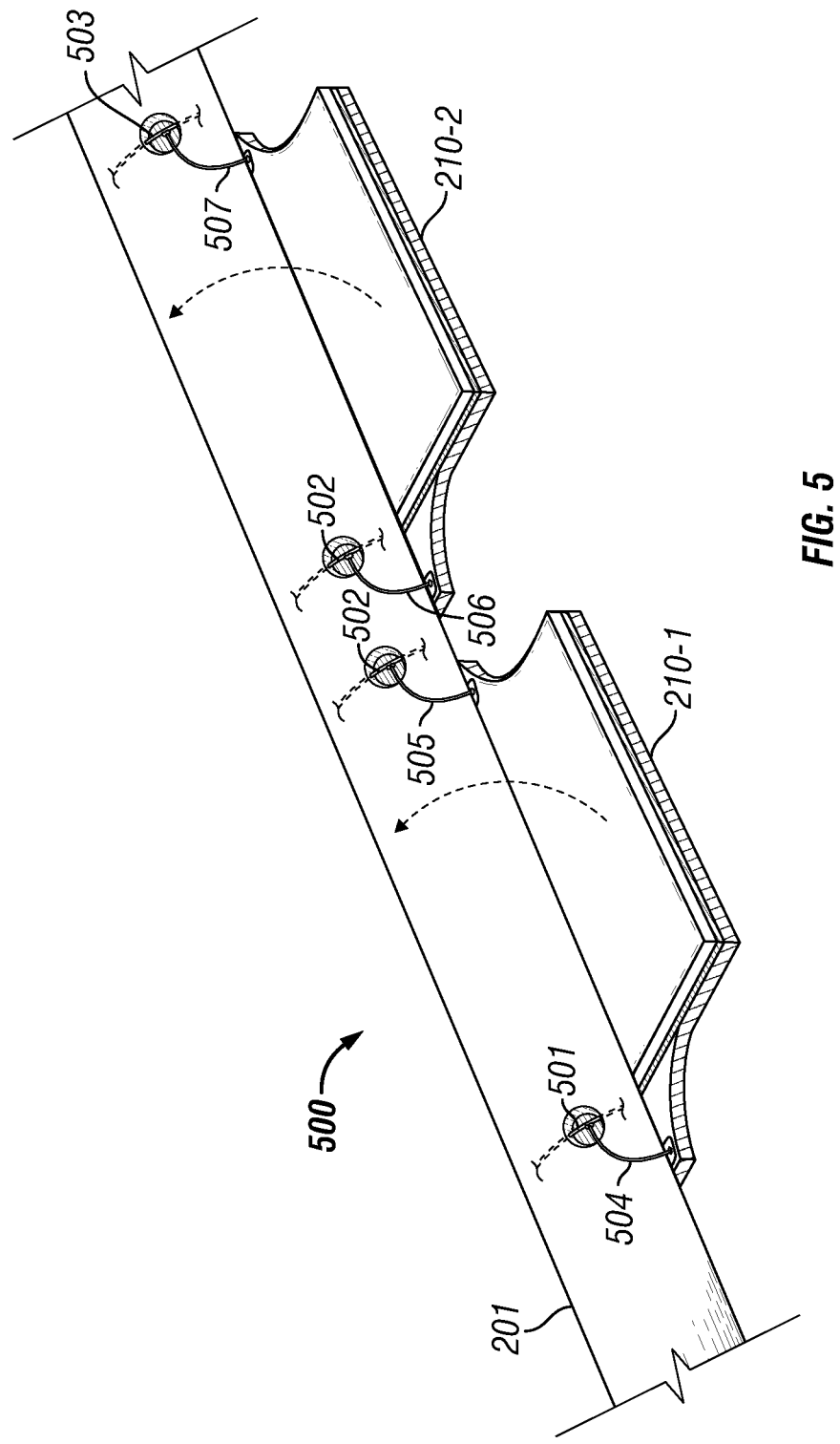
FIG. 5 depicts electrode assemblies connected to a lead body to implement the circuit shown in FIG. 4.

FIG. 5 depicts electrode assemblies 210 connected to lead body 201 to implement the circuit shown in FIG. 4. As is known in the art, wire conductors embedded with lead body 201 are typically helically wound and are accessible at many locations along lead body 201. Some representative embodiments utilize the helical arrangement of wire conductors to couple an electrode assembly 210 to multiple wire conductors to capacitively couple adjacent electrodes together. Specifically, as shown in lead segment 500 of FIG. 5, the electrode portion of electrode assembly 210 is coupled to wire conductor 501 of lead body 201 through jumper wire 504. Wire conductor 501 is also coupled to a terminal (not shown) at the proximal end of lead body 201. The interior metal component of electrode assembly 210-1 is coupled to wire conductor 502 through jumper wire 505. Wire conductor 502 is also coupled (at another location) through jumper wire 506 to the electrode of electrode assembly 210-2. Wire conductor 502 connects the electrode of electrode assembly 210-2 to another terminal (not shown) at the proximal end of lead body 201. In a similar manner, the interior metal component of electrode assembly 210-2 is coupled to wire conductor 503 (through jumper wire 507) that is used to connect the next electrode to a terminal.

Figure 6:
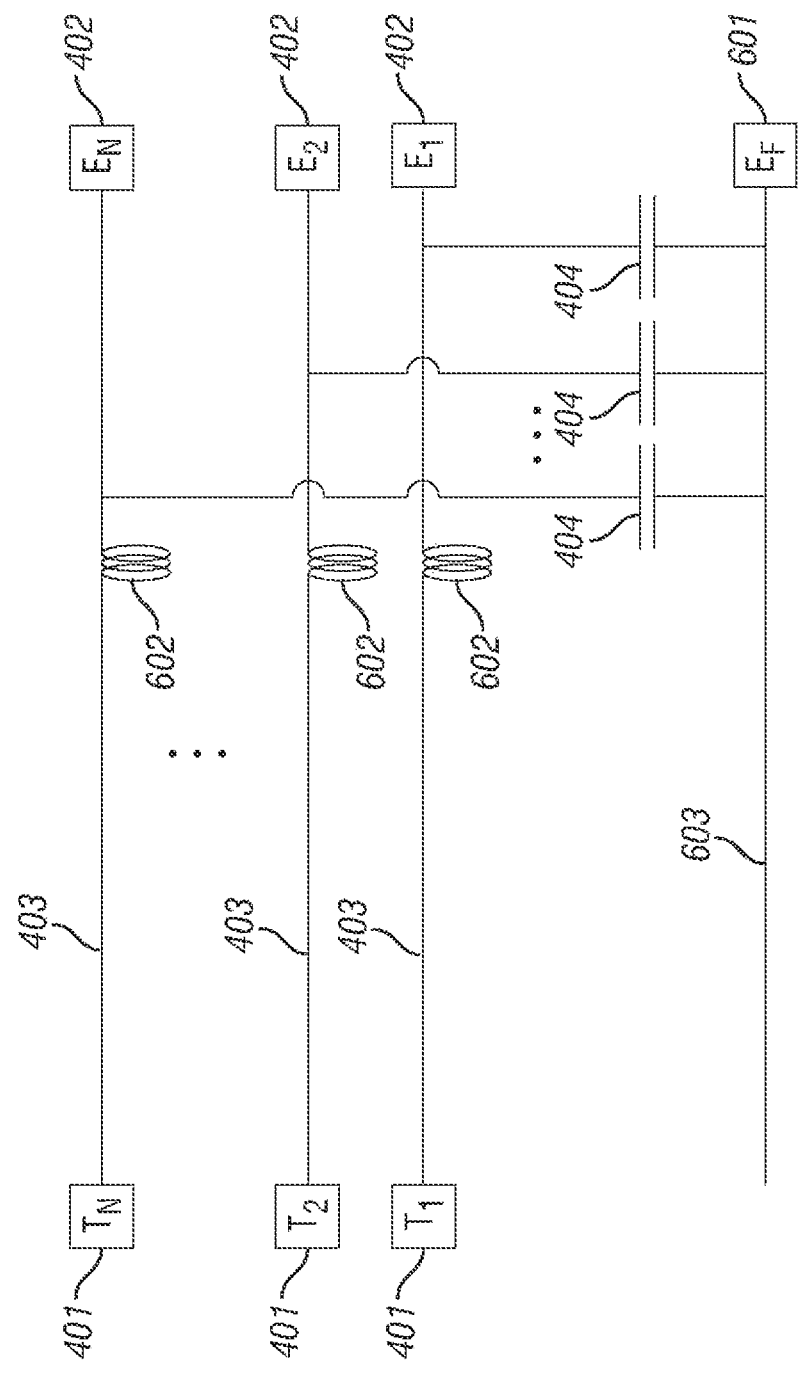
FIG. 6 depicts a circuit for mitigating MRI induced current according to an alternative embodiment.

FIG. 6 depicts circuit 600 for mitigating MRI induced current according to an alternative embodiment. Circuit diagram 600 depicts a plurality of terminals 401 ($T_1$-$T_N$) electrically coupled to a plurality of electrodes 402 ($E_1$-$E_N$) through lead wires 403. Additionally, inductors 602 are disposed between lead wires 403 and electrodes 402 to limit the current flowing there between at high frequencies. Specifically, the inductance of inductors 602 is preferably selected such that relatively little attenuation occurs at stimulation frequencies while a relatively high amount of attenuation occurs at MRI frequencies. In addition, the electrodes 402 ($E_1$-$E_N$) are coupled through capacitors 404 to line 603 which leads to floating electrode 601 ($E_F$). The capacitance of capacitors 404 is preferably selected such that the impedance is relatively high at stimulation frequencies while the impedance is relatively low at MRI frequencies. Floating electrode 601 preferably provides a relatively large surface area relative to the other electrodes 402. At MRI frequencies, the MRI induced current will be distributed over a greater surface area and any accompanying temperature rise in patient tissue will be reduced.

Figure 7:
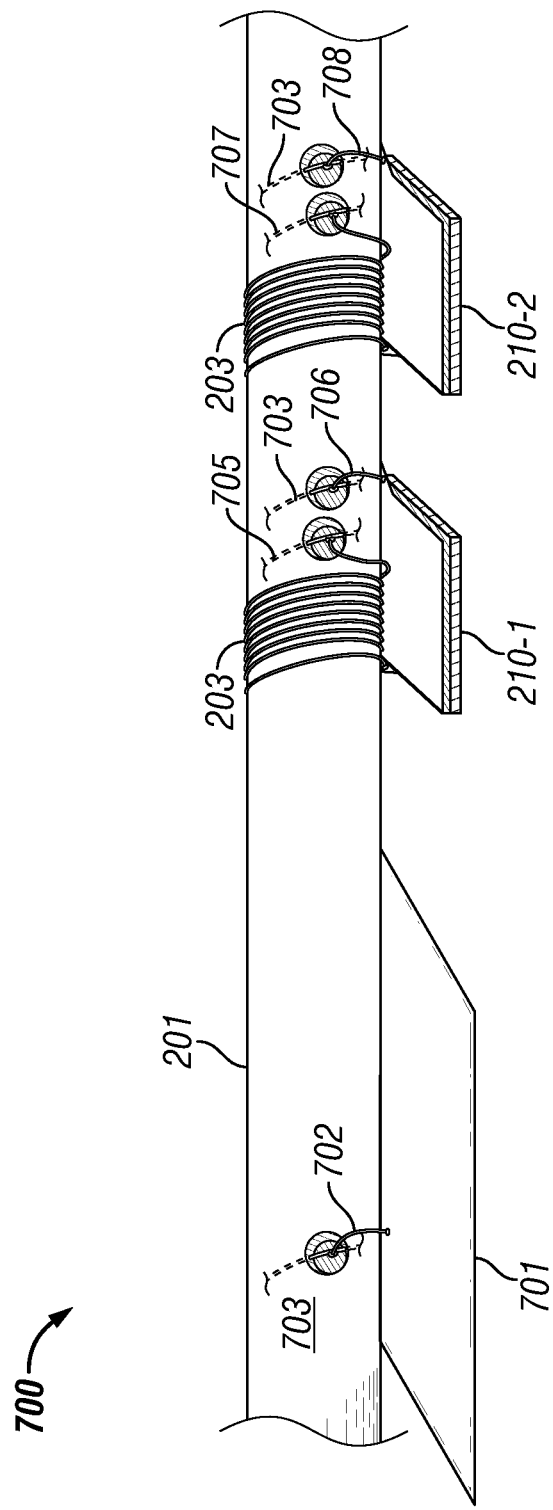
FIG. 7 depicts a lead for implementing the MRI filtering circuitry shown in FIG. 6 according to one representative embodiment.

FIG. 7 depicts lead 700 for implementing the MRI filtering circuitry shown in FIG. 6 according to one representative embodiment. As shown in FIG. 7, lead 700 comprises floating electrode 701 that possesses a relatively large surface area. Floating electrode 701 is coupled to wire conductor 703 that is embedded within lead body 201 using jumper wire 702. Wire conductor 703 need not necessarily be coupled to a terminal on the proximal end of lead body 201. Lead 700 further comprises a plurality of electrodes assemblies 210 (shown as 210-1 and 210-2). Wire conductor 705, embedded within lead body 201, is coupled to one end of thin wire 203. The other end of thin wire 203 is coupled to the electrode portion of electrode 210-1. The interior metal component of electrode assembly 210-1 is coupled to wire conductor 703 of lead body 201 using jumper wire 706. Electrode assembly 210-2 is disposed in substantially the same manner as electrode assembly 210-1. The electrode portion of electrode assembly 210-2 is coupled to one end of thin wire 203. The other end of thin insulated wire 203 is coupled to wire 707, which is embedded in lead body 201. Also, the interior metal component of electrode assembly 210-2 is coupled to wire 703 of lead body 201 using jumper wire 708.

FIG. 14 depicts stimulation system 1400 according to one representative embodiment. Neurostimulation system 1400 includes pulse generator 1420 and one or more stimulation leads 1401. An example of a commercially available pulse generator is the EON® implantable pulse generator available from Advanced Neuromodulation Systems, Inc. Pulse generator 1420 is typically implemented using a metallic housing that encloses circuitry for generating the electrical pulses for application to neural tissue of the patient. Control circuitry, communication circuitry, and a rechargeable battery (not shown) are also typically included within pulse generator 1420. Pulse generator 1420 is usually implanted within a subcutaneous pocket created under the skin by a physician.

Lead 1401 is electrically coupled to the circuitry within pulse generator 1420 using header 1410. Lead 1401 is used to conduct the electrical pulses from the implant site of the pulse generator for application to the targeted nerve tissue via electrode assemblies 1410. For example, the distal end of lead 1401 may be positioned within the epidural space of the patient to deliver electrical stimulation to spinal nerves to treat chronic pain of the patient. Also, an "extension" lead (not shown) may be utilized as an intermediate connector if deemed appropriate by the physician. Electrode assemblies 1450 are preferably coupled to the conductor wires of lead 1450 in a manner that reduces MRI induced current or otherwise mitigates MRI heating. Any of the electrode assemblies and circuit designs discussed herein may be used for assemblies 1450 and lead 1401.

Some representative embodiments may provide a number of advantages. Some representative embodiments provide an efficient fabrication methodology for inclusion of MRI current mitigating components within a stimulation lead. For example, some representative embodiments do not complicate the lead body of stimulation lead to accommodate passive MRI mitigating components as seen in some proposed MRI compatible lead designs. Additionally, some representative embodiments provide partial shielding for a magnetic core of the inductor, if needed, thereby reducing distortion within MRI imaging caused by the stimulation lead.

Although some embodiments have been described in terms of neurostimulation systems, the present application is not limited to such systems. For example, leads for cardiac applications (e.g., pacing, defibrillation, etc.) could be adapted to mitigate MRI induced current for alterative embodiments.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed:

1. A method of fabricating a percutaneous stimulation lead for applying electrical stimulation to tissue of a patient, comprising:
    providing a lead body of insulative material that comprises a plurality of conductors within the insulative material;
    fabricating a plurality of terminals on a proximal end of the lead body; and
    fabricating a plurality of electrode assemblies on a distal end of the lead body, wherein (i) each electrode assembly of the plurality of electrode assemblies comprises a first layer, a second layer, and a third layer, (ii) the first layer and second layer being formed from a respective continuous wire, (iii) the third layer comprising a ring of conductive material, and (iv) the fabricating comprises:
        (a) wrapping the respective continuous wire without an insulative material about the lead body to form the first layer of a respective electrode assembly; and
        (b) continuing to wrap the respective continuous wire with an insulative material about the first layer to form the second layer;
    wherein each second layer of the plurality of electrode assemblies forms an inductor and each first layer of the plurality of electrode assemblies and each corresponding third layer are capacitively coupled.

2. The method of claim 1 wherein wrapping comprises:
    applying mechanical processing to the continuous wire to remove the insulative material from the continuous wire.

3. The method of claim 1 wherein wrapping comprises:
    applying laser processing to the continuous wire to remove the insulative material from the continuous wire.

4. The method of claim 1 wherein the continuing to wrap comprises:
    applying the insulative material to the continuous wire; and
    applying energy to cure the insulative material as the second layer is being formed.

5. The method of claim 1 further comprising:
    electrically coupling each continuous wire with a respective conductor of the lead body.

6. The method of claim 1 further comprising:
    welding a distal end of each continuous wire to a respective corresponding ring of conductive material.

7. The method of claim 1 wherein each electrode assembly forms a respective electrical circuit that filters an MRI-induced current.

8. The method of claim 1 wherein the first layer is wrapped with adjacent turns of the continuous wire being in mechanical contact.

* * * * *